United States Patent [19]

Boulikas

[11] Patent Number: 5,894,060
[45] Date of Patent: Apr. 13, 1999

[54] CLONING METHOD FOR TRAPPING HUMAN ORIGINS OF REPLICATION

[76] Inventor: Teni Boulikas, 249 Matadero Ave., Palo Alto, Calif. 94036

[21] Appl. No.: 08/884,025

[22] Filed: Jun. 27, 1997

Related U.S. Application Data

[60] Provisional application No. 60/023,110, Jun. 28, 1996.

[51] Int. Cl.[6] .................................................. C12Q 1/68
[52] U.S. Cl. ................................................................. 435/6
[58] Field of Search ................................ 435/6, 172.3

[56] References Cited

PUBLICATIONS

Linskens et al., *Cell*, vol. 62, pp. 845–847, 1990.
Boulikas, Teni, "Homeotic protein binding sites, origins of replication, and nuclear matrix anchorage sites share the ATTA and ATTTA motifs", Journal of Cellular Biochemistry 50 (1992) 111–123.
Boulikas, Teni, "Poly (ADP–ribose) synthesis in blocked and damaged cells and its relation to carcinogenesis", Anticancer Research 12 (1992) 885–898.
Boulikas, Teni, "Nature of DNA sequences at the attachment regions of genes to the nuclear matrix", Journal of Cellular Biochemistry 55 (1994) 513–529.
Boulikas, Teni, "Homeodomain protein binding sites, inverted repeats, and nuclear matrix attachment regions along the human β–globin gene complex", Journal of Cellular Biochemistry 52 (1993) 23–36.
Boulikas, T. et al., "Multitude of inverted repeats characterizes a class of anchorage sites of chromatin loops to the nuclear matrix", Journal of Cellular Biochemistry 53 (1993) 1–12.

Boulikas, Teni, "Transcription factor binding sites in the matrix attachment region (MAR) of the chicken α–globin gene", Journal of Cellular Biochemistry 55 (1994) 513–529.
Boulikas, Teni, "A model of transcription/replication enhancers (Review)", Oncology Reports 2 (1995) 171–181.
Boulikas, Teni, "The phosphorylation connection to cancer (Review)", Int'l Journal of Oncology 6 (1995) 271–278.
Boulikas, Teni, "How enhancers work: juxtapositioning of DNA control elements by synergistic interaction of MARs (Review–Hypothesis)", Int'l Journal of Oncology 6 (1995) 1313–1318.

*Primary Examiner*—James Ketter
*Attorney, Agent, or Firm*—Peter J. Dehlinger

[57] ABSTRACT

A method of identifying a DNA sequence containing a human origin of replication (hORI) is disclosed. The method includes the steps of (A) providing fragments of human genomic DNA suitable for cloning into a bacterial plasmid, (B) ligating the fragments into a bacterial plasmid comprising (i) a bacterial origin of replication, (ii) a bacterial selection marker, and (iii) a mammalian selection marker, (C) transforming bacterial host cells with the plasmid, (D) selecting transformed bacterial host cells using the bacterial selection marker, (E) isolating plasmid DNA from the transformed bacterial host cells, (F) transfecting human cells with the isolated plasmid DNA, (G) selecting transfected human cells using the mammalian selection marker, (H) isolating extrachromosomal DNA from selected human cells, (I) digesting a suspension of the extrachromosomal DNA with a restriction endonuclease capable of cleaving methylated, but not unmethylated DNA, and (J) purifying undigested extrachromosomal DNA from the suspension.

20 Claims, 1 Drawing Sheet

| Step 1: | A human genomic structure (1 million base pairs) containing 7 ORIs (boxes) |
|---|---|
| Step 2: | Digestion with restriction endonucleases |
| Step 3: | Cloning into the plasmid vector. Only the plasmids containing the ORIs (boxes) will be selected by the human cells |

CLONING METHOD FOR TRAPPING HUMAN ORIGINS OF REPLICATION

This application claims the benefit of U.S. Provisional Application Ser. No. 60/023,110, filed Jun. 28, 1996, incorporated herein by reference.

FIELD OF THE INVENTION

The present invention relates to a method of cloning human origins of replication (ORIs).

References

Anachkova, B., and Hamlin, J. L., *Mol. Cell. Biol.* 9:532-540 (1988).
Ariga, H., et al., *Mol. Cell. Biol.* 5:563-568 (1985).
Ariga, H., et al., *EMBO J.* 8:4273-4279 (1989).
Ausubel, F. M., et al., *Current Protocols in Molecular Biology* (John Wiley and Sons, Inc., Media, Pa.).
Bergemann, et al., *Mol. Cell. Biol.* 12:5673-5682 (1992).
Blumenthal, A. B., et al., *Cold Spring Harbor Symp. Quant. Biol.* 38:205-223 (1974).
Borowiec, J. A., and Hurwitz, J., *EMBO J.* 7:3149-3158 (1988).
Boulikas, T., and Kong, C. F., *Int. J. Oncol.* 2:325-330 (1993a).
Boulikas, T., and Kong, C. F., *J. Cell. Biochem.* 53:1-12 (1993b).
Boulikas, T., *Biochem. Cell Biol.* 64:474-484 (1985).
Boulikas T., *Biochem. Cell Biol.* 64:463-473 (1986).
Boulikas, T., *EMBO J.* 7:57-67 (1988).
Boulikas, T., *J. Mol. Evol.* 35:156-180 (1992).
Boulikas, T., *J. Cell. Biochem.* 5223-36 (1993).
Boulikas, T., *Oncol. Rep.* 2:171-181 (1995a).
Boulikas, T., *Int. Rev. Cytol.* 162A:279-388 (1995b)
Boulikas, T., *J. Cell. Biochem.* 60:297-316 (1996).
Boye, E., and Løbner-Olesen, A., *Cell* 62:981-989 (1990).
Brewer, B. J., and Fangman, W. L., *Cell* 51:463-371 (1987).
Brewer, B. J., and Fangman, W. L., *Cell* 55:637-653 (1988).
Brown, E. H., et al., *Mol. Cell. Biol.* 7:450-457 (1987).
Burhans, W. C., et al., *Biochemistry* 25:441-449 (1986).
Burhans, W. C., et al., *Cell* 62:955-965 (1990).
Callan, H. G., *Cold Spring Harbor Symp. Quant. Biol.* 38:195-203 (1974).
Carroll, S. M., et al., *Mol. Cell. Biol.* 7:1740-1750 (1987).
Carroll, S. M., et al., *Mol. Cell. Biol.* 13:2971-2981 (1993).
Cassileth, et al., *Human Gene Therapy*, 6:369-383 (1995).
Classon, et al., *Nature* 330:272-274 (1987).
Cockerill, P. N., and Garrard, W. T., *Cell* 44:273-282 (1986).
Cockerill, P. N., *Nuc. Acids Res.* 18:2643-2648 (1990).
Collins, et al., *EMBO J.* 12:4555-4566 (1993).
Copeland, W. C., and Wang, T. S. -F., *J. Biol. Chem.* 266:22739-22748 (1991).
Deb, S. P., et al., *Mol. Cell. Biol.* 6:1663-1670 (1986a).
Deb., S. P., et al., *Mol. Cell. Biol.* 6:4578-4584 (1986b).
Deb., S. P., and Tegtmeyer, P., *J. Virol.* 61:3649-3654 (1987).
Delidakis, C., and Kafatos, F. C., *EMBO J.* 8:891-901 (1989).
Dhar, V., et al., *Mol. Cell. Biol.* 8:4958-4965 (1988).
DiMaio, et al., *Proc. Natl. Acad. Sci. USA* 79:4030-4034 (1982).
Dubey, D. D., et al., *Mol. Cell. Biol.* 11:5346-5355 (1991).
Edenberg, H. J., and Huberman, J. A., *Ann. Rev. Genet.* 9:245-284 (1975).
Erdile, I. G., et al., *J. Biol. Chem.* 266:12090-12098 (1991).
Frappier, L., and Zannis-Hadjopoulos, M., *Proc. Natl. Acad. Sci. USA* 84:6668-6672 (1987).
Giri, et al., *Virology* 127 p. 385 (1983).
Goldman, M. A., et al., *Science* 224:686-692 (1984).
Hand, R., *Cell* 15:317-325 (1987).
Handeli, S., et al., *Cell* 57:909-920 (1989).
Hatton, K. S., et al., *Mol. Cell. Biol.* 8:2149-2158 (1988).
Hay, R. T., and DePamphilis, M. L., *Cell* 28:767-779 (1982).
Heinzel, S. S., et al., *Mol. Cell. Biol.* 11:2253-2272 (1991).
Hendrickson, W. G., et al., *Cell* 30:915-923 (1982).
Hirt, B., *J. Mol. Biol.* 26365-369 (1967).
Holmquist, G. P., *Am. J. Hum. Genet.* 40:151-173 (1987).
Huberman, J. A., and Riggs, A. D., *J. Mol. Biol.* 32:327-342 (1968).
Huberman, J. A., et al., *Cell* 51:473-481 (1987).
Iguchi-Ariga, S. M. M., et al., *EMBJ J.* 6:2365-2371 (1987a).
Iguchi-Ariga, S. M. M., et al., *Nuc. Acids Res.* 15:4889-4899 (1987b).
Iguchi-Ariga, S. M. M., et al., *EMBO J* 7:3135-3142 (1988).
Iguchi-Ariga, S. M. M., et al., *Biochim. Biophys. Acta* 1172:73-81 (1993).
Kitsberg, D., et al., *Nature* 366:588-590 (1993).
Krysan, P. J., et al., *Mol. Cell. Biol.* 9:1026-1033 (1989).
Krysan, P. J., and Calos, M. P., *Mol. Cell. Biol.* 11:1464-1472 (1991).
Landry, S., and Zannis-Hadjopoulos, M., *Biochim. Biophys. Acta* 1088:234-244 (1991).
Leffak, M., and James, C. D., *Mol. Cell. Biol.* 9:586-593 (1989).
Leu, T. H., and Hamlin, J. L., *Mol. Cell. Biol.* 9:532-540 (1989).
Linskens, M. H. K., and Huberman, J. A., *Cell* 62:845-847 (1990).
Little, R. D., et al., *Mol. Cell. Biol.* 13:6600-6613 (1993).
Maniatis, T., et al., in *MOLECULAR CLONING: A LABORATORY MANUAL*, Cold Spring Harbor Laboratory, Cold Spring Harbor, N.Y. (1982).
Martin, R. G., and Oppenheim, A., *Cell* 11:859-869 (1977).
Mastrangelo, I. A., et al., *Nature* 38:658-662 (1989).
Meneguzzi, et al., *EMBO J.* 3 p. 365 (1984).
Nierendorf, R. C., and Pfeffer, D., *Meth. Enz.* 152:556-562 (1987).

Mitrani-Rosenbaum, et al., *Mol. Cell Biol.* 3 p. 233 (1983).

Montiel, J. F, et al., *Nuc. Acids Res.* 12:1049–1068 (1984).

Ogden, G. B., et al., *Cell* 54:127–135 (1988).

Parsons, R. E., et al., *J. Virol.* 64:509–518 (1990).

Parsons, R. E., et al., *J. Virol.* 65:2798–2806 (1991).

Pearson, C. E., et al., *EMBO J.* 14:1571–1580 (1995).

Rao, B. S., et al., *Gene* 87:233–242 (1990).

Rassoulzadegan, M., et al., *Proc. Natl. Acad. Sci. USA* 8:4354–4358 (1983).

Rivier, D .H., and Rine, J., *Science* 256:659–663 (1992).

Rose, S. M., and Garrard, W. T., *J. Biol. Chem.* 259:8534–8544 (1984).

Roth, G. E., et al., *Mol. Cell. Biol.* 3:1898–1908 (1983).

Ruiz, J. C., et al., *Mol. Cell. Biol.* 9:109–115 (1989).

Ruley, H. E., *Nature* 304:602–606 (1983).

Russell, D. W., and Zinder, N. D., *Cell* 50:1071–1079 (1987).

Sambrook, J., e t al., *MOLECULAR CLONING: A LABORATORY MANUAL*, Second Edition, Cold Spring Harbor Laboratory (Cold Spring Harbor, N.Y.) (1989).

Smithies, O., *J. Cell. Physiol. Cuppl.* 1:137–143 (1982).

Sollner-Webb, B., et al., *Cell* 14:611–627 (1978).

Spradling, A., and Orr-Weaver, T., *Annu. Rev. Genet.* 21:373–403 (1987).

Taira, T., et al., *Mol. Cell. Biol.* 14:6386–6397 (1994).

Taylor, H. J., *Chromosoma* 62:291–300 (1977).

Taylor, H. J., *Mol. Cell. Biochem.* 61:99–109 (1984).

Thierry, A. R., et al., *Proc. Natl. Acad. Sci USA* 92:9742–9749 (1995).

Trempe, J. P., et al., *Mol. Cell. Biol.* 8:1657–1663 (1988).

Tsurimoto, T., and Stillman, B., *Mol. Cell. Biol.* 9:609–619 (1989a).

Tsurimoto, T., andStillman, B., *EMBO J.* 8:3883–3889 (1989b).

Umekawa, et al., *J. Biochem* 104:333–336 (1988).

Vassilev, L., and Johnson, E. M., *Nuc. Acids Res.* 17:7693–7705 (1989).

Vassilev, L., and Johnson, E. M., *Mol. Cell. Biol.* 10:4899–4903 (1990).

Vaughn, J. P., et al., *Cell* 61:1075–1087 (1990).

Villarreal, L. P., *Microbiol. Rev.* 55:512–542 (1991).

Wu, R., et al., *Meth. Enzymol.* 152:343–349 (1987).

Zannis-Hadjopoulos, M., et al., *Mol. Cell. Biol.* 5:1621–1629 (1985).

Zhu, N., et al., *Science* 261:209–211 (1993).

BACKGROUND OF THE INVENTION

A great deal of our knowledge on origins of replication (ORIs) comes from the study of ORIs in animal viruses. The SV40 and polyomavirus origins of replication occur in highly accessible, nucleosome-free regions of about 450 base pairs (bp) which are activated by T antigen protein encoded by the viral genome. This nucleosome-free gap contains both transcription and replication controlling elements. Large T antigen alone (90 kDa) initiates each round of viral DNA synthesis. However, several transcription factors are known to bind to the 21 bp repeats and the 72 bp enhancers of the SV40 ORI; these transcription factors could interact with large T to enhance initiation of replication.

Three rather extensive regions within SV40 ORI, termed sites I, II and III, bind large T (Hay 1982). The SV40 core ORI consists of three domains of a total length of 64 bp: (i) a sequence with an imperfect inverted repeat; (ii) a palindrome with four GAGGC pentanucleotide repeats recognized by T antigen; and (iii) a 17-bp A-Trich segment (Deb, et al., 1986a; Parsons, et al., 1990). T antigen contacts and melts bases in the imperfect inverted repeat, structurally distorts the GAGGC pentanucleotide domain the bends and untwists the AT-rich domain (Deb, et al., 1986b; Borowiec and Hurwitz, 1988; Parsons, et al., 1990). All three domains of core ORI are protected by the T antigen toward digestion by DNase I (Deb and Tegtmeyer, 1987).

In the presence of ATP twelve molecules of large T antigen are assembled in the form of two hexamers on the SV40 core ORI (Mastrangelo, et al., 1989; Tsurimoto, et al., 1989a, 1989b). Assembly of a hexamer first occurs on the early half core ORI and then on the late half; the formation of these hexamers melts the early ORIs and untwists the late half core ORIS; melting and untwisting releases large T antigen molecules from the GAGGC pentanucleotides to act as helicases at flanking DNA regions (Parsons, et al., 1991).

The B subunit of DNA polymerase a (68 kDa) mediates the assembly of the 180 kDa subunit with T antigen acting as a molecular tether linking the two proteins (Collins, et al., 1993). Thus, T antigen enhances the ability of DNA polymerase α to prime the synthesis of new DNA chains and to extend pre-existing DNA chains (Erdile, et al., 1991; Collins, et al., 1993). In the absence of T antigen DNA polymerase a synthesizes about 7–13 nt per binding event and then dissociates from DNA (Copeland and Wang, 1991); the ability of T antigen to translocate in the 3' to 5' direction along the DNA in an ATP-consuming process and the linkage of T antigen to the 180 kDa catalytic subunit of DNA polymerase α via the 70 kDa B subunit would be expected to hold the polymerase and make single-stranded template available, thus increasing enzyme processivity (Collins, et al., 1993).

Unlike *E. coli*, which uses a single start point to replicate its DNA, eukaryotic cells use multiple replication origins (Huberman and Riggs, 1968; Linskens and Huberman, 1990). The existence of multiple replicons—chromosomal segments that are replicated from a single origin and whose size, number and temporal order of replication is cell type- and developmental stage-specific (Edenberg and Huberman, 1975; Hand, 1978)—has promoted the idea of chromatin compartmentalization into domains. The 300 kb locus comprising the murine immunoglobulin heavy chain gene segments is a single replicon (Brown, et al., 1987).

Both RNA and DNA viruses, using either prokaryotic or eukaryotic cells for their proliferation, usually possess a unique, and in some cases (i.e., HSV), two or three origins of replication. For example, both the DNA of SV40, a virus causing cancer in monkeys (5 kb), and the genome of *E. coli* $(3 \times 10)^6$ bp) are replicated from a single origin. However, eukaryotes, due to their vast content in DNA, require multiple origins in replication. For example, the genome of the fruit fly *Drosophila melanogaster* ($\sim 10^8$ bp) and the DNA in haploid human nuclei ($\sim 3 \times 10^9$ bp) use about 5,000 and 60,000 start points of DNA replication, respectively.

Of the 60,000 or so ORIs from human cells, five specific ORIs have apparently been identified as of June 1996. The known human ORIs are:

(i) That of the β-globin gene complex (Kitsberg, et al., 1993; Boulikas, 1993). Earlier studies on the replication of the β-globin multigene cluster showed temporal directionality and led to the identification of potential initiation sites for the replication of the β-globin gene complex (Dhar, et al., 1988);

(ii) that of the c-myc gene (Iguchi-Ariga, et al., 1988; Ariga, et al., 1989; Vassilev and Johnson, 1990);

(iii) the ORI in the 18S/28S ribosomal DNA 44 kb repeating unit (Little, et al., 1993);

(iv) the ORI of the human HSP70 gene (Taira, et al., 1994); and (v) the ORI of the CHAT gene (Boulikas, et al., 1996).

These ORIs are presumably activated by transcription factors (TFs) and replication initiator proteins which may include ssDNA-binding proteins (Bergemann, et al., 1992) and cruciform DNA-binding proteins (Pearson, et al., 1995). One TF involved in replication initiation may be the oncoprotein c-myc which promotes cellular DNA replication by binding to a cloned human putative ORI sequence (Iguchi-Ariga, et al., 1987a), c-myc can substitute for SV40 large T-antigen in an in vitro SV40 replication system (Iguchi-Ariga, et al., 1987b; Classon, et al., 1987). A region approximately 2 kb upstream of the transcription start site of the human c-myc gene contains a putative ORI of 210 bp (Boulikas, 1996, herein incorporated by reference) which is also a transcription enhancer containing c-myc binding sites (Iguchi-Ariga, et al., 1988a; Umekawa, et al., 1988). This fragment contains the 22-nucleotide binding site determined by DNase footprinting and mobility shift assays; this interaction is involved in both upregulating transcription as well as replication of the c-myc gene domain (Ariga, et al., 1989).

DNA sequences enriched in origins of replication termed ors have been isolated by extrusion of single-stranded newly synthesized DNA at the replication fork from actively replicating monkey cells in culture (Zannis-Hadjopoulos et al., 1985). pBR322 plasmid harboring several cloned ors sequences have been shown to be autonomously and extrachromosomally replicating after their transfection into HeLa cells (Frappier and Zannis-Hadjopoulos, 1987; Rao et al, 1990; Landry and Zannis-Hadjopoulos, 1991).

Two chromosomal origins of replication within the DHFR amplicon (240 kb) mapped by two different approaches (Anachkova and Hamlin, 1988; Leu and Hamlin, 1989) are located at a distance of about 20 kb from one another. One of these origins had been localized in a 4.3 kb fragment (Burhans, et al., 1986) and was narrowed down to a 450 bp fragment by mapping the site where the strand specificity of the Okazaki fragments switches (Burhans, et al., 1990). The presence of two independent origins for the amplified DHFR locus was confirmed by Handeli, et al. (1989) using a novel mapping procedure. Multiple initiation sites are apparently used for the replication of this gene repeat lying within a 28 kb region (Vaughn, et al., 1990). These data do not contradict the model that precise DNA sequences are used for the initiation of DNA replication in mammalian cells since ~1000 copies of the DHFR gene that may include DNA elements that function in replication initiation are present within an amplicon.

Plasmids carrying the cad gene and flanking regulatory sequences were able to function as autonomously replicating episomes in mammalian cells (Carroll, et al., 1987). A bidirectional origin in the native locus and in episomally amplified murine adenosine deaminase loci has been found (Carroll, et al., 1993). The region of DNA replication in the murine immunoglobulin heavy chain gene has been identified and the octamer motif has been suggested as a putative DNA replication origin in mammalian cells (Iguchi-Ariga, et al., 1993). Similar studies are consistent with the presence of a replication origin in the mdr-1 gene (Ruiz, et al., 1989). The chicken has one H5 gene displaying a polarity with respect to its replication in expressing and non-expressing cell types; these data are compatible with an origin in the 5' flanking region used for the replication of the avian β-globin gene in erythroid cells and from an origin in the 3' flanking region in nonerythroid cell types (Trempe, et al., 1988). Shot-gun cloning experiment aimed at identifying mammalian genomic sequences with ARS activity in yeast has identified autonomously replicating sequences (Roth, et al., 1983; Montiel, et al., 1984; Ariga, et al., 1985).

SUMMARY OF THE INVENTION

In one aspect, the invention includes a method of identifying a DNA sequence containing a human origin of replication (hORI) is disclosed. The method includes the steps of (A) providing fragments of human genomic DNA suitable for cloning into a bacterial plasmid, (B) ligating the fragments into a bacterial plasmid comprising (i) a bacterial origin of replication, (ii) a bacterial selection marker, and (iii) a mammalian selection marker, (C) transforming bacterial host cells with the plasmid, (D) selecting transformed bacterial host cells using the bacterial selection marker, (E) isolating plasmid DNA from the transformed bacterial host cells, (F) transfecting human cells with the isolated plasmid DNA, (G) selecting transfected human cells using the mammalian selection marker, (H) isolating extrachromosomal DNA from selected human cells, (I) in a suspension containing said extrachromosomal DNA, cleaving bacterially-synthesized DNA. The uncleaved extrachromosomal DNA in the suspension comprises a DNA sequence containing a human origin of replication. Such uncleaved extrachromosomal DNA may be purified from the suspension and/or used to transform host cells for amplification of the plasmid.

In one general embodiment, the fragments of human genomic DNA are generated by digestion of human genomic DNA with a suitable restriction endonuclease (e.g., EcoRI). The fragments may also be produced by other DNA fragmentation methods, including sonication and shearing by passage through a narrow-bore syringe needle.

The fragments typically have an average size of more than about 100 base pairs (bp) in length and less than about 10 kbp in length. Preferably, the average size is between about 2 kbp and about 6 kbp in length (e.g., 4 kbp).

The plasmid may be any plasmid suitable for transforming bacterial cells, though it is typically a pUC-derived or pBR322-derived plasmid (see, e.g., Sambrook, et al., or Ausubel, et al., for a description of bacterial plasmids). The bacterial origin of replication (ORI) may be, for example, a pUC or pBR322 ORI. The bacterial host cells are preferably *E. coli* cells.

The bacterial selection marker can be any of a variety of known bacterial selectable markers, such a gene conferring resistance to a selected antibiotic. Examples of such antibiotics (and corresponding genes) include ampicillin (β-lactamases), tetracycline, chloramphenicol (chloramphenicol acetyltransferases), and kanamycin (kanamycin phosphotransferases).

Competent bacterial cells may be transformed with the plasmid using any standard bacterial cell transformation method, including calcium chloride transformation or electroporation. See, for example, Ausubel, et al., Chapter 1, for methods of making competent cells and methods for introducing plasmids into bacterial cells.

Similarly, the mammalian selection marker can be selected from any of a variety of mammalian selectable markers. Examples of such markers include adenosine deaminase (ADA), aminoglycoside phosphotransferase (neo, APH), dihydrofolate reductase (DHFR), hygromycin-b-phosphotransferase (HPH), thymidine kinase (TK), and xanthine-guanine phosphoribosyltransferase (XGPRT, gpt). Selection conditions for the above markers can be found, e.g., in Ausubel, et al., Chapter 9. A preferred mammalian selection marker is aminoglycoside phosphotransferase, a neomycin-resistance gene. Cells possessing plasmids containing this gene are preferably selected using neomycin or G418 (geneticin).

Any of a variety of different human cells or cell lines may be used in the transfection step. Exemplary human cells suited for such transfection are K562 human erythroleukemia cells. As above, the transfection may be carried out using any known method of mammalian cell transfection. Such methods include calcium phosphate transfection, transfection using DEAE-dextran, liposome-mediated transfection, and electroporation. Preferred transfection methods are liposome-mediated transfection using cationic liposomes and electroporation.

Extrachromosomal DNA may be isolated from transfected human cells using, for example, the Hirt extraction method.

The suspension of extrachromosomal DNA is typically cleaved by digestion with a restriction endonuclease capable of cleaving methylated (typically at adenine residues), but not unmethylated DNA. An exemplary restriction endonuclease capable of cleaving methylated, but not unmethylated DNA, is DpnI.

As stated above, the uncleaved extrachromosomal DNA comprises a DNA sequence containing a human origin of replication. In one general embodiment of the invention, this uncleaved extrachromosomal DNA is used for a second round of transfection and selection according to steps (F)–(J), above.

These and other objects and features of the invention will become more fully apparent when the following detailed description is read in conjunction with the accompanying drawings.

DETAILED DESCRIPTION OF THE INVENTION

I. Multiple ORIs in Higher Eukaryotes

Figure 1:
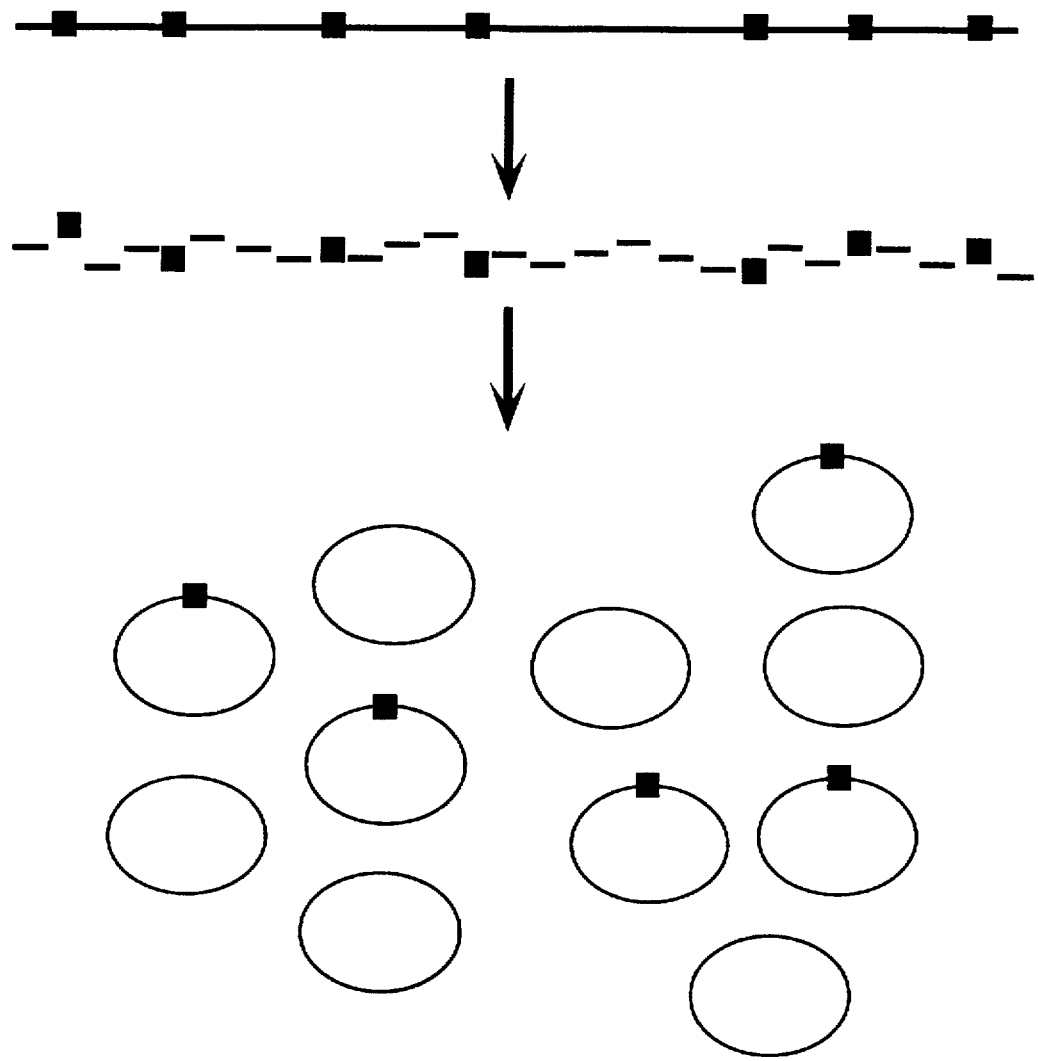
FIG. 1 is a schematic diagram of the method of the invention.

According to the present invention, the observations summarized above can be reconciled by the following model: higher eukaryotes, due to the higher sequence complexity of replication origins, have developed a more sophisticated mechanism for firing specific sets of origins than the more simple genomes of viruses, bacteria, and mitochondria; replication enhancers, proposed to coincide with transcriptional enhancers, act synergistically with a core origin to enhance the efficiency of initiation of DNA replication (Boulikas, et al., 1995a, 1995b, herein incorporated by reference). Like transcription, requiring more than one enhancer (e.g., three enhancers and one promoter in the case of the histone H5 gene; Rousseu, et al., 1993), origin in higher eukaryotes may similarly require more than one enhancer occasionally located at a large distance from the core ORI. Thus, the longer the fragment of DNA dissected from the human genome in the range of 10–20 kb, the higher the probability of finding enhancer elements cooperating with the core origin.

This model reconciles the studies of Calos and coworkers (Heinzel, et al., 1991; Krysan and Calos, 1991; Krysan, et al., 1989) finding that large fragments from the human genome can confer autonomous replication with studies showing that small defined genomic fragments in the size range of 500 bp from primates can drive the episomal replication of bacterial plasmids in humans cells (Zannis-Hadjopoulos, et al., 1995; Frappier and Zannis-Hadjopoulos, 1987; Iguchi-Ariga, et al., 1988; Ariga, et al., 1989; Rao, et al., 1990; Landry, et al, 1991). In these studies the particular plasmid used (defective EBV, pBR322 Bluescript, etc.) and the transfected cell type may have a role in autonomous replication. A special case in such discrepancies are amplified genes like the chorion genes in fruit flies (Delidakis and Kafatos, 1989) and the DHFR amplicon in CHO cells expected to possess multiple origins or truncated origins and although initiating their replication at various sites along the genomic DNA nevertheless may use the same DNA sequence characteristics.

About 50,000 origins of replication are thought to be present in each nucleus in mammalian cells during all developmental stages; some are used at early and others at later stages of development (Spradling and Orr-Weaver, 1987). In addition, a fraction of ORIs, linked with housekeeping genes, is presumably active at all stages of development. Thus, a net decrease in the number of active ORIs takes place during development (Callan, 1974). Origins of transcriptionally active genes are "fired" during early S-phase; this is in contrast to the heterochromatin and transcriptionally inactive genes which are replicated in late S-phase (Holmquist, 1987; Dhar, et al., 1988). The activation of replication origins during the early versus mid and late- S-phase of the cell cycle is governed by some unknown mechanism which seems to be associated with the transcription status of a gene and its attachment to the nuclear matrix.

II. Matrix-Attached Regions (MARs)

Matrix-attached regions (MARs) are responsible for the structuring of genomes into chromatin domains. Specific interactions between DNA sequence motifs on MARs and matrix proteins are responsible for the formation of the boundaries of chromatin units. Specifically, MARs (together with matrix proteins) constrain polynuceosomes into loops or domains, thereby insulating them from the effects of chromatin structure and torsional strain from flanking domains. MAR sequences have an average size of 500 bp, are spaced about every 30 kb, and are believed to harbor or lie next to the origins of replications (ORIs) of the eukaryotic genome.

Matrix proteins comprise one type of MAR-associating proteins. The MAR-associating proteins include (i) the classical matrix proteins, not displaying a strict DNA sequence specificity but rather a preference for AT-rich motifs (lamins A, B, topoisomerase II, histone Hi, Nuc2$^+$, SAF-A, SATB1, nucleoli, matrins, calmodulin); (ii) a number of transcription factors (NF-1, ATF, Sp1, AP-1, C/EBP, RFP, T antigen, steroid hormone receptors, Tat of HIV, E7 of HPV-16); (iii) transcriptional adaptors such as retinoblastoma; (iv) a number of enzymes (histone deacetylases, casein kinase II, DNA polymerase $\alpha$ and $\beta$); (v) intermediate filaments; (vi) hnRNA protein components; and (vii) the Ser-Arg family of protein splicing factors (see Table II in Boulikas, 1995, herein incorporated by reference).

The presence of this complex assortment of structural and regulatory molecules in the matrix, some of which play an important role in DNA replication and transcription, as well as overwhelming evidence from analysis of MAR structures and in situ localization of DNA replication and transcription complexes together indicate that the nuclear matrix plays a fundamental, unique role in nuclear processes and that the structuring of genomes into domains has a functional significance.

III. Activation and Silencing of Origins of Replication

A program of specific silencing of origins of replication may drive the differential gene expression and the establishment of cell memory during development. The early Xenopus embryo, for example, increases the number of replication origins in order to replicate its genome within 10 to 15 minutes (Callan, 1974). A similar process has been found in Drosophila embryos (Blumenthal et al., 1974). During subsequent stages of development different origins of replication may be suppressed in different cell types. This resembles the differential gene expression as well as the pattern of DNA methylation, starting from fully unmethylated DNA in the fertilized egg.

The mammalian genome contains more ORIs than actually needed for its replication at a particular stage of development; the number of active origins decreases with pattern and cell type determination during development (Spradling, et al. 1987). As development proceeds, different replication origins, which are supposed to be anchored to the nuclear matrix, might be activated with a concomitant decrease in the total number of active origins. Thus, the multiplicity of origins may drive the differential gene expression and cell type formation during embryogenesis (Taylor, 1977, 1984; Brown et al., 1987; Hatton et al., 1988).

IV. Replicons

Replicons may physically coincide with large chromatin domains formed by the permanent class of MARs. According to the present invention, large domains may be subdivided into smaller subdomains by the facultative class of MARS. In line with this proposal, the entire 300 kb region encompassing the murine immunoglobulin heavy chain gene region was found to be a single replicon (Brown et al., 1987). Yet, this region was determined to contain multiple matrix anchorage sites spaced every 20 to 70 kb (Cockerill, 1990).

Martin and Oppenheim (1977) found that the average fork-to-fork distances in SV40-transformed Chinese hamster lung cells were shorter, or that there were more forks per unit length of DNA in transformed compared to nontransformed cells of the same type: The mean replicon size of the transformed cells was about 31 mm as compared with ~44 mm for the nontransformed cells. Since 10 bp of DNA have a length of 3.4 nm, then the $3 \times 10^9$ bp of the Chinese hamster genome have a length of 1.02 m. If the length of the DNA ($1.02 \times 10^6$ mm) is divided by the size of the replicon (31 or 44 mm), we obtain ~33,000 replicons per haploid genome for transformed and ~23,200 replicons per haploid genome for normal cells. It was thought that the T antigen, coded by SV40 and acting as an initiator of host DNA synthesis, was responsible for the increase in the number of replication initiation sites during transformation of cells by SV40.

Replication enhancers are defined as DNA elements that interact with the core origin to enhance manyfold replication efficiency. This interaction is via proteins bound to the enhancer region with proteins bound to the core ORI and looping out of DNA. Core ORI by itself functions as a transcriptional enhancer for the gene(s) in the same chromatin loop. One core ORI may require more than one transcription enhancers for its activation. Replication specificity is conferred by a class of replication initiator proteins, comprising cruciform-binding proteins, that need to interact with transcription factors at the core ORI for origin firing; transcription specificity is provided by the interaction of the transcription/replication enhancer with the immediate 5' flanking promoter region. Core ORIs in this model possess a great number of transcription factor binding sites in addition to the initiator protein sites; both initiator proteins and transcription factors cooperate in origin firing. The developmental programs leading to inactivation of specific genes during cell type formation are proposed to be tightly linked with programs leading to the inactivation of ORIS; thus active ORIs are also active enhancers whereas inactive ORIs are linked with transcriptionally-inactive genes and are identical to enhancers inactivated during development or differentiation. Tumor cells are expected to be able to assemble a larger number of active enhancers because of activation of early embryo- or fetal stage-specific transcription factors, resulting in the activation of early developmental stage-specific ORIS.

The capacity of papillomaviruses for autonomous extrachromosomal replication into the appropriate host (DiMaio, et al., 1982; Mitrani-Rosenbaum, et al., 1983; Giri, et al., 1983; Meneguzzi, et al., 1984) has prompted the identification of DNA sequence elements in their genome able to maintain this function for human and animal gene therapy or cell culture transfection studies. A fragment of 69% of the BPV1 genome, after deletion of the L1 and L2 sequences coding for major structural proteins of the virus, has been used to drive the episomal expression of IL-2 cDNA under control of the murine metallothinein promoter in human SCLC cells in ex vivo studies; the 69% fragments contains the E1 to E8 early genes and regulatory regions including its origin of replication (see Cassileth, et al., 1995).

Several cloning vectors able to episomal replication have been constructed which use the SV40 or the related polyoma virus ORI and the T-antigen cDNA to express the T antigen protein in human or animal cells and effect the episomal replication of the plasmid containing the SV40 ORI (Zhu, et al., 1993; Thierry, et al., 1995). However, T antigen exerts profound effects on host gene regulation leading to deregulation of cell growth, known as transformation (although, on the other hand, the polyoma large T antigen has not been shown to cause oncogenic transformation but to facilitate the establishment of embryo fibroblasts as permanent cell lines (Rassoulzadegan, et al., 1983) and to cooperate with other oncogenes in the tumorigenic transformation of primary cells (Ruley, 1983).

It is desirable for human gene therapy applications to use natural human ORIs in order to drive the episomal replication of therapeutically important genes. To-date, due to our incomplete knowledge of human sequences able to act as ORIs no vectors with human ORIs have been used in gene therapy.

Experiments performed in support of the present invention on the human CHAT gene ORI indicate that this ORI can be used to construct episomal plasmids that might find application in human gene therapy. The use of human ORIs is desirable over viral ORIs used in gene transfer to somatic cells (Zhu, et al., 1993; Thierry, et al., 1995) that seem to require the presence of a viral replication initiator protein cDNA in the same vector for the episomal retention of the plasmid. The rather small size of this human ORI (513 bp or 1435 bp if fragments C,D, and E are combined together) makes it attractive for use with retroviral or adenoviral and AAV vectors because of their limited payload capacity.

V. Method for Isolating Human ORIs

A methodology is described for isolating human sequences with strong origin of replication (ORI) activity. Human genomic DNA is isolated and digested with restriction endonucleases into fragments of an average size of about 4 kb. Alternatively, the human genomic DNA used is 1% of total DNA attached to the nuclear matrix, known to be enriched in human ORIs.

The DNA fragments are then ligated into a bacterial plasmid which cannot replicate in human cells, containing neomycin and ampicillin resistance genes. The ligation mixture is used to transform competent *E. coli* cells (such as strain DH5α) and clones are grown on ampicillin/neomycin plates. Resistant clones are isolated and used to make a plasmid DNA prep, which contains a mixture of several hundred thousand different recombinant plasmid molecules.

Human sequences with ORI function are selected by transfection of the mixture of the recombinant plasmids into human cells in culture, in the presence or absence of 1 mg/ml of G418 (geneticin) for selecting transfected cells expressing the plasmid. Episomal and extrachromosomal plasmids are extracted from the human cells at 3 days and 30 days posttransfection. The plasmids are treated with DpnI, which destroys the bacterially-replicated plasmids to eliminate input plasmid DNA. The DpnI-resistant plasmids are used to transform *E. coli* cells and to isolate individual colony plasmids.

The total plasmid isolate may be subjected into a second cycle of transfection into human cells in culture and selection of the extrachromosomally-replicating plasmids. Individual clones selected in this way can drive the autonomous replication of selected heterologous genes (e.g., therapeutically important human genes in cells in vivo and in vitro, and are useful in human gene therapies.

The isolated ORIs can further be used in footprinting assays of transcription/replication factors to identify the regions of interaction with MAR-associating proteins. Further, oligonucleotides from these regions, immobilized on Sepharose beads, can be used to react with a mixture of transcription/replication factors isolated from human cells to identify their corresponding proteins in binding assays. This approach may be used to isolate novel nuclear proteins involved in the activation of human ORIs.

The following example is intended to illustrate but in no way limit the invention.

Materials and Methods

Reagents such as restriction enzymes, modifying enzymes, and the like may be purchased from a variety of commercial suppliers, including New England Biolabs (Beverly, Mass.), United States Biochemical (USB; Cleveland, Ohio), Boehringer Mannheim (Indianapolis, Ind.), and Strategene (La Jolla, Calif.).

A. Isolation and Nuclear Matrix Preparation

Nuclei are isolated using the procedure of Boulikas (1988). According to this method, cultured cells are lysed in 1% Triton X-100 and nuclei are collected by centrifugation through a 60% glycerol cushion at 13,000×g for 4 minutes in "EPPENDORF" tubes (Boulikas, 1988). Nuclei isolated from $2.5 \times 10^7$ cells are digested with 1,000 units micrococcal nuclease (MNase) at 37° C. for 10 minutes in 0.5 ml 50 mM Tris.HCl, pH 7.5, 25 mM KCl, 1 mM $CaCl_2$, 4 mM $MgCl_2$.

Nuclear matrices are isolated by an adaptation of the methods of Cockerill and Garrard (1986) and Boulikas (1986). All procedures are at 0° C. in the continuous presence of 0.1 mM N-p-tosyl-L-lysine chloromethyl ketone to minimize proteolysis and in "EPPENDORF" tubes using short-time spins to avoid nuclear matrix disaggregation. According to this method, digested nuclei are centrifuged in "EPPENDORF" tubes for 2 minutes in a microfuge (13,000×g) to yield a supernatant fraction S1, enriched in active chromatin (Rose and Garrard, 1984). The pellet (P1), containing digested nuclei, is then lysed in 0.5 ml 2 mM EDTA, 3 mM Tris, pH 7.5, and the lysed nuclei are centrifuged at 13,000×g for 3 minutes.

The supernatant fraction (S2) of the lysed nuclei centrifugation contains the bulk of nucleosomes mainly as mononucleosome particles due to the extensive treatment with MNase. The pellet fraction, P2, containing the residual of the chromatin loops and the nuclear matrix, is resuspended in 0.5 ml 2M NaCl, 2 mM EDTA, 10 mM Tris, pH 7.5, and immediately centrifuged (3 minutes) to separate the residual histones from the nuclear matrix (NM) fraction. The DNA content of the nuclear matrix fraction that can be monitored by the extent of digestion of nuclei by MNase (Boulikas, 1985) typically represents 1–2 % of total DNA and typically has fragments ranging in size from 0.1–5.0 kb (Boulikas and Kong 1993a,b). The nuclear matrix fraction is resuspended in 0.2 ml 5M urea. Then 0.2 ml 2% SDS is added and the nuclear matrix proteins are removed with proteinase K (0.1 mg/ml), at 37° C. for 16 hours. DNA is extracted twice with phenol/chloroform and precipitated with 70% ethanol. NM DNA preparations are size-fractionated on agarose gels and purified using Qiagen columns for cloning.

B. Agarose Gel Electrophoresis

The various nuclear fractions are adjusted to 1% SDS, 10% glycerol, 0.05% bromophenol blue in TBE buffer (89 mM Tris, 89 mM boric acid, pH 8.5, 1 mM EDTA) and loaded directly onto 1% agarose gels containing 10 µg/ml ethidium bromide, 0.1% SDS in TBE buffer. The electrophoresis buffer is TBE buffer containing 0.1% SDS.

C. Cloning of the Nuclear Matrix DNA in pBlueScript

Pieces from the low-melting agarose gel containing 100–700 bp or 0.7–5.0 kbDNA fragments and about 3 µg of nuclear matrix DNA are excised under low-energy UV light. Exposure to UV is minimized to avoid formation of cyclobutane dimers and (6–4) photoproducts on the DNA that cause C→T transitions during replication (see Boulikas, 1992).

One volume of TE buffer (10 mM Tris, pH 8.0, 1 mM EDTA) is added to the gel piece, melted at 65° C., extracted once with phenol, once with phenol/chloroform, once with chloroform, and precipitated by the addition of 2 vol. ethanol and 0.1 vol. of 3M sodium acetate at −70° C. overnight in Eppendorf tubes.

DNA is collected by centrifugation at 0° C. for 20 minutes (13,000×g, microfuge), washed in 70% ethanol and resuspended in 20 µl TE. In some experiments the DNA fragments are phosphorylated at their 5' ends using T4 polynucleotide kinase (GIBCO/BRL, Grand Island, N.Y.) and ATP as described (Wu, et al., 1987). The 3' recessed ends generated by MNase (Sollner-Webb, et al., 1978) are filled in with 1 µl (4 units) Klenow fragment of DNA polymerase in TE buffer, extracted with 1 vol. phenol, once with phenol/chloroform and ethanol-precipitated.

The DNA pellet is dried in a Speedvac for 5 min, resuspended in 7 µl $H_2O$, 1 µl 10× ligation buffer, 1 µl "BLUESCRIPT" vector (Stratagene, La Jolla, Calif.) cut with EcoRV, and 1 µl T4 ligase (USB) and incubated at 14° C. for 16 hours. DNA is directly transformed in JM109 or DH5α competent *E. coli* cells and plated on LB/agar with ampicillin (100 µg/ml), X-gal and IPTG. Plates are incubated at 37° C. overnight and screened for white colonies. Individual colonies are picked and grown in 3 ml LB + ampicillin (100 µg/ml). Plasmid minipreps digested with EcoRI + HindIII are analyzed for the size of the insert on 1% agarose gels.

A family of new vectors is constructed containing the neomycin resistance gene, the lacZ gene of *E. coli* encoding β-galactosidase, and a polylinker whereupon cloning of a MAR/ORI insert would cause disruption of the b-galactosisdase gene and loss of the blue color in colonies, and the kanamycin-resistance gene. Cloning in such vectors is performed using standard methods (e.g., Maniatis, et al., 1982; Sambrook, et al., Ausubel, et al.).

E. DNA Sequencing

DNA sequencing is performed using the dideoxy method and the Sequenase II kit (USB). For this purpose, double-stranded DNA plasmid is denatured, mixed with universal or reverse primers (USB), and DNA strand synthesis is performed according to the manufacturer's instructions and the method of Mierendorf and Pfeffer (1987). The sequencing reaction DNA is analyzed on gels (4% acrylamide, 50% w/v urea, 60 cm long, 0.4 mm thick) by running at about 65 Watts for 2.5–3 hours. The gels are dried on Whatman 3 MM filter paper and exposed for autoradiography for about 24 hours at room temperature using X-Omat film.

F. DpnI Assays and Bromodeoxyuridine Incorporation

Fragments of DNA isolated using the methods of the invention can be tested for their efficacy in driving the autonomous replication of a bacterial plasmid after its introduction into cells in culture in transient transfection experiments. A preferred method for testing replication of a DNA fragment in higher eukaryotes is the DpnI-resistance assay on Hirt extracts (Hirt, 1967) at 48–72 post-transfection. According to this method, cells are lysed with SDS in the presence of about 0.5 M NaCl; the lysate is left at 0° C. for several hours. Under these conditions high molecular weight genomic DNA forms a large complex with the SDS-NaCl complex which can be removed following centrifugation at 13,000 to 25,000×g for about 30 minutes–1 hour, leaving the low size plasmid or viral DNA in the supernatant (Hirt, 1967). The plasmid DNA in the supernatant is extracted, digested with DpnI, the fragments are separated by electrophoresis on agarose gels, and blotted on nylon or nitrocellulose filters using the bacterial plasmid as a probe. DpnI-resistant plasmids are those replicated in eukaryotic cells and lacking methylation on adenine residues characteristic of molecules replicated in *E. coli*. Only bacterially-made DNA that carries methylated A that is cleaved by DpnI (Frappier and Zannis-Hadjopoulos, 1987).

Although identification of a genomic sequence that confers autonomous replication to a plasmid does not guarantee that the sequence will function as an origin of replication in vivo., most sequences capable of driving the extrachromosomal replication have sequence motifs characteristic of ORIs and could be used as origins at a certain developmental stage or cell type.

Another method for determining autonomous replication is from the incorporation of the heavy bromodeoxyuridine in place of thymidine in the newly synthesized DNA followed by isolation of low molecular weight DNA (Hirt, 1967) and separation of the heavy and light extrachromosomal DNA by CsCl density gradient centrifugation (Frappier and Zannis-Hadjopoulos, 1987).

G. Two-Dimensional Mapping Techniques

The development of two-dimensional agarose gel electrophoresis on neutral/neutral (Brewer and Fangman, 1987) or neutral/alkaline (Huberman, et al., 1987) gels has prompted the identification of origins of replication. Replication intermediates (forks, bubbles, q-shaped or Cairns structures) from the yeast 2 mm plasmid terminate in multiply interlocked catenanes and are subsequently resolved by the cell machinery to monomer plasmids; restriction fragments derived from the Cairns structures contain replication forks and bubbles that are separated from one another and from nonreplicated linear DNA by low voltage agarose gel electrophoresis which resolves DNA primarily by mass, followed by a second dimensional gel electrophoresis in a higher percentage gel and at a higher voltage, separating DNA by shape as well as by mass (Brewer and Fangman, 1987).

According to the procedure of Huberman, et al. (1987), replication intermediates from 2 mm plasmid of yeast are separated on neutral agarose gels which are further separated by size and into nascent and parental strands on the second dimensional alkaline agarose gels. Closed circular, nicked circular, full-length linear, as well as oligomers of these forms give discrete spots on 2D gels. Transfer of the DNA fragments from the 2D gels onto nylon membrane filters and hybridization with short probes from different areas of the suspected replication origin reveals the direction of fork movement (Huberman, et al., 1987). If a particular genome-derived restriction fragment does not contain an origin of replication, the replication intermediates of this fragment will be fork-shaped, because a replication fork will proceed through the fragment from one end to the other; genomic probes from the origin of replication will reveal the presence of bubble-shaped replication intermediates arising from two forks proceeding bidirectionally from the origin. Fork-shaped versus bubble-shaped intermediates give rise to different arc patterns on 2D gel blots (Brewer and Fangman, 1987, 1988; Rivier and Rine, 1992). Since replicating DNA represents a small fraction of total DNA, especially in asynchronous cell cultures, these analyses can be facilitated by selective adsorption of the partially single-stranded DNA of replication intermediates on benzoylated naphthoylated DEAE-cellulose (Huberman, et al., 1987).

The 2D agarose gel technique does not have sufficient resolution to determine whether initiation occurs at a single site or from multiple dispersed or closely spaced ORIs present over a small genomic region in the range of 500 bp.

EXAMPLE 1

Isolation of Human ORI sequences

Human genomic DNA is isolated and digested with restriction endonucleases into fragments of an average size of approximately 4 kb; the fragments are inserted into cloning vectors which contain: (i) a bacterial plasmid ORI permitting replication in *E. coli* such as pUC or pBR322 ORI (ii) the ampicillin-resistance gene allowing selection of the plasmids in *E. coli* cells; (iii) a neomycin-resistance gene near the cloning site to be driven by the cloned human sequence; (iv) the firefly luciferase gene in the opposite orientation from the neomycin-resistance gene and on the other side of the cloning site to be driven by the same human DNA sequence element; (v) the LacZ gene containing the cloning site and the Sp6/T7 promoters at the flanks of the cloning site allowing white/blue colony selection after treatment of bacteria with IPTG and X-Gal in order to identify the plasmids with human sequence inserts forming white colonies (FIG. 1).

The ligation mixture is used to transform competent *E. coli* cells (such as strain DH5α), the total transformed population of cells is cultured, and plasmids are isolated. The resulting plasmid prep is a mixture of several hundred thousand different plasmid molecules which, upon electrophoresis on agarose gels, give a smear with size range higher than that of the control plasmid without insert. At this stage, it is possible to size-fractionate the plasmids from the gel and pursue the cloning of large, medium, and small inserts separately.

The plasmid preparation is purified using Qfagen plasmid purification columns, complexed with cationic liposomes (e.g., the commercially available lipofectin or transfectam), and is used to transfect K562 human erythroleukemia cells. Selection of the proper cell line is important since different cell types use a subset of different ORIs for the replication of their genome (Boulikas 1995a).

The plasmid mixture is introduced into the cells, the cell culture is split into two, and the cells are cultured in the presence or absence of G418 (1 mg/ml). This antibiotic is destroyed by those human cells which express the neomycin-resistance gene. Such cells are able to expand during culturing. Thus, a selection of the human DNA sequences able to drive the neomycin-R gene is made at this stage.

A further selection is performed for plasmids capable episomal (extrachromosomal) replication in human cells in view of the function of the insert as an ORI. Episomally replicated plasmids are isolated from the human cultured cells using, e.g., the Hirt extraction method (1967), and treated with DpnI, which digests only the plasmids which have been replicated in E. coli cells (DpnI recognizes the GATC tetranucleotide only when the A is methylated). Only bacteria (not human or other eukaryotic) cells can methylate A in this sequence. This tetranucleotide is recognized by dam methyltransferase which methylates the adenine residue at the $N^6$ position.

The plasmids that have been replicated in human cells and that survive DpnI digestion contain human sequences able to function as ORIs in the host mammalian cells. Such a plasmid isolate is used to transform E. coli; total plasmid DNA is isolated, and can optionally be subjected to a second round of transfection of human cells and selection. Individual clones are isolated as white colonies from IPTG/X-Gal smeared agar plates. Bacteria are grown from individual colonies, the plasmid is isolated, the insert is sequenced using the Sp6/T7 primers, and its ORI function is tested using three different approaches (i) the ability to sustain the episomal replication in human cells after transfection of the plasmid; (ii) using the PCR method of Vassilev and Johnson (1989); and (iii) using the two-dimensional mapping approach (Huberman, et al., 1987) Clones isolated using the above protocol are expected to represent or contain human ORIs. Such sequences may be used, for example, in plasmid vectors for driving the episomal replication of therapeutically important genes in animal tissues after in vivo injection and in human tissues in clinical trials.

It is claimed:

1. A method of identifying a DNA sequence containing a human origin of replication (hORI), comprising (A) providing fragments of human genomic DNA suitable for cloning into a bacterial plasmid, (B) ligating said fragments into a bacterial plasmid comprising (i) a bacterial origin of replication, (ii) a bacterial selection marker, and (iii) a mammalian selection marker, (C) transforming bacterial host cells with said plasmid, (D) selecting transformed bacterial host cells using said bacterial selection marker, (E) isolating plasmid DNA from said transformed bacterial host cells, (F) transfecting human cells with said isolated plasmid DNA, (G) selecting transfected human cells using said mammalian selection marker, (H) isolating extrachromosomal DNA from selected human cells, (I) in a suspension containing said extrachromosomal DNA, cleaving bacterially-synthesized DNA, wherein uncleaved extrachromosomal DNA in said suspension comprises a DNA sequence containing a human origin of replication.

2. The method of claim 1, wherein said fragments of human genomic DNA are generated by digestion of human genomic DNA with a restriction endonuclease.

3. The method of claim 1, wherein said fragments have an average size of more than about 100 base pairs (bp) in length.

4. The method of claim 1, wherein said fragments have an average size of less than about 10 kbp in length.

5. The method of claim 4, wherein said fragments have an average size of between about 2 kbp and about 6 kbp in length.

6. The method of claim 1, wherein said plasmid is a pUC-derived or pBR322-derived plasmid.

7. The method of claim 1, wherein said bacterial origin of replication (ORI) is a pUC or pBR322 ORI.

8. The method of claim 1, wherein said bacterial host cells are E. coli cells.

9. The method of claim 1, wherein said bacterial selection marker is an ampicillin-resistance gene.

10. The method of claim 1, wherein said mammalian selection marker is a neomycin-resistance gene.

11. The method of claim 1, wherein said human cells are K562 human erythroleukemia cells.

12. The method of claim 1, wherein said transfecting is done using cationic liposomes.

13. The method of claim 1, wherein said transfecting is done using electroporation.

14. The method of claim 1, wherein said isolating extrachromosomal DNA is done using Hirt extraction method.

15. The method of claim 1, wherein said cleaving of step (I) is accomplished by digesting a suspension of said extrachromosomal DNA with a restriction endonuclease capable of cleaving methylated, but not unmethylated DNA.

16. The method of claim 15, wherein said restriction endonuclease capable of cleaving methylated, but not unmethylated DNA, is DpnI.

17. The method of claim 15, wherein said methylated DNA is methylated at adenine residues.

18. The method of claim 1, wherein said bacterial plasmid in ligation step (B) further comprises a firefly luciferase gene oriented opposite to the neomycin-resistance gene.

19. The method of claim 1, wherein said bacterial plasmid in ligation step (B) further comprises a LacZ gene containing a cloning site flanked on one end by an Sp6 promoter and on the other by a T7 promoter.

20. The method of claim 1, wherein said undigested extrachromosomal DNA obtained in step (J) is used for a second round of transfection and selection according to steps (F)–(J) of claim 1.

* * * * *